United States Patent [19]

Lord

[11] 4,332,564
[45] Jun. 1, 1982

[54] PREFABRICATED MODULAR CROWN SYSTEM

[76] Inventor: Raymond E. Lord, 418 Church St., North Adams, Mass. 01247

[21] Appl. No.: 116,091

[22] Filed: Jan. 28, 1980

[51] Int. Cl.³ .............................................. A61C 5/08
[52] U.S. Cl. ..................................... 433/218; 433/223
[58] Field of Search ............... 433/223, 219, 222, 218; 264/19

[56] References Cited

U.S. PATENT DOCUMENTS

| | | | |
|---|---|---|---|
| 424,050 | 3/1890 | Curtis | 433/222 |
| 1,444,436 | 2/1923 | Teeter | 433/223 |
| 2,700,822 | 2/1955 | Infante | 433/222 |
| 2,930,124 | 3/1960 | Pos | 433/223 |
| 2,930,125 | 3/1960 | Pos | 433/223 |
| 3,375,582 | 4/1968 | Myerson | 433/223 |
| 3,541,688 | 11/1970 | McLean et al. | 433/222 |
| 3,793,728 | 2/1974 | Corbineau | 433/219 |

Primary Examiner—Gene Mancene
Assistant Examiner—John J. Wilson

[57] ABSTRACT

Two preformed modules are manipulated and joined onto a natural tooth stump to constitute a crown which provides the combination of full facial esthetics with the utility and durability of a metal crown. Splinting of adjacent teeth and addition of pontic teeth is also accomplished at chairside in conjunction with a routine office-laboratory procedure.

5 Claims, 4 Drawing Figures

U.S. Patent   Jun. 1, 1982   4,332,564
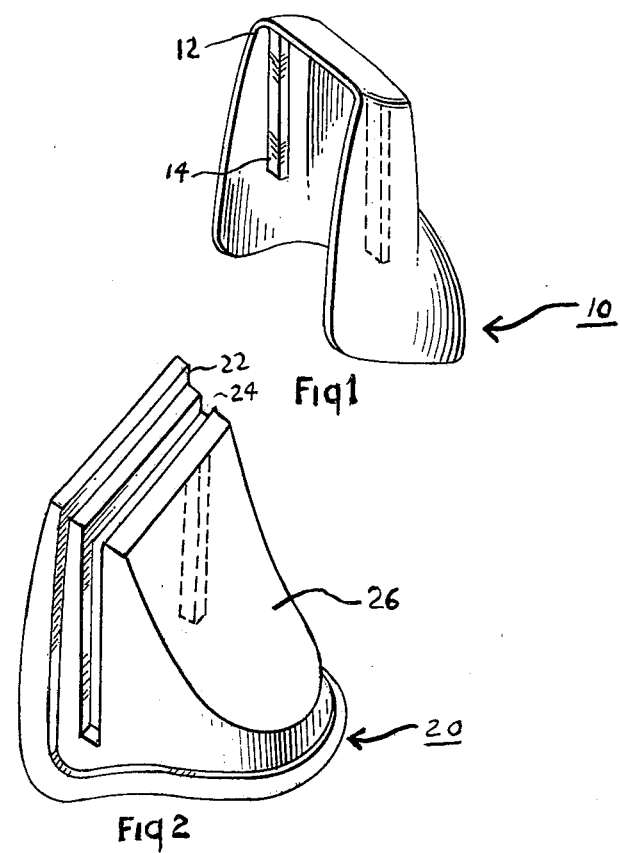
Fig 1
Fig 2
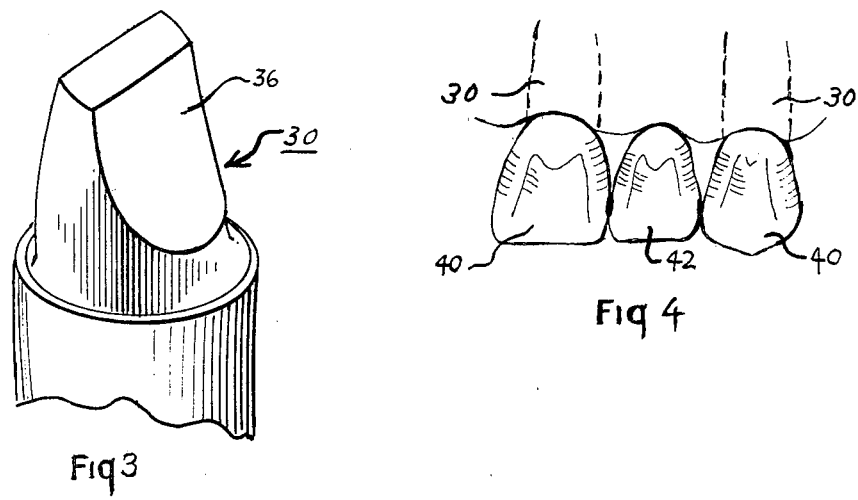
Fig 3
Fig 4

4,332,564

PREFABRICATED MODULAR CROWN SYSTEM

BACKGROUND OF THE INVENTION

This invention relates to a modular full crown system, and more particularly to such a system permitting both direct or indirect construction of the crown.

Direct placement of crowns involves only procedures that may be performed at chairside. Indirect placement involves procedures that require laboratory work in addition to chairside work.

Attempts have been made in the prior art with prefabricated facings (esthetic) and prefabricated metal backings. These systems satisfy esthetics and function, but: (1) the connection of the two parts during construction is achieved with difficulty; and (2) splinting with accuracy is accomplished more by accident than determination.

SUMMARY OF THE INVENTION

An object of this invention is to provide a full crown system for application of a combination crown (i.e., esthetic module and functional module) at chairside during a single office visit. Another object is to provide full crown coverage that facilitates the splinting of two or more teeth. A third object is the replacement of a missing tooth by the use of dummy modules. A fourth object is the provision of a combination of prostheses, i.e., partial denture planning in combination with splinting.

The crowns of this invention are not limited to particular teeth in the dental arch, but rather have universal application for restorative usages.

In accordance with this invention, a full crown system employs two separate modules. An esthetic module is fitted to the prepared tooth stump in a manner to be described. After fitting, or even after final cementation of the esthetic module is complete, a function module is cemented to the esthetic module in place.

BRIEF DESCRIPTION OF THE DRAWING

FIG. 1 is a perspective of a functional module of this invention.

FIG. 2 is a perspective of an esthetic module of this invention.

FIG. 3 is a perspective of a prepared tooth stump.

FIG. 4 is an elevation showing the splinting of a pontic or dummy tooth between crowns of this invention.

DESCRIPTION OF THE PREFERRED EMBODIMENTS

In general, the modular full crown system of this invention provides full coverage of a tooth by a combination of two modular members so as to restore both function and esthetics. The functional module preferably is made of metal and the esthetic module preferably is made of a plastic or other suitable esthetic material.

This modular crown system combines the strength of preformed metal on all wear surfaces (mesial, distal, lingual and incisal or occlusal) with the esthetic or facial (labial) surface being of a plastic material resembling a natural tooth. Both modules are preformed and are joined into a single combination crown at chairside. Splinting and bridging are accomplished by soldering or welding the metallic modules of adjacent members. In addition, splinting and bridging are easily accomplished due to the accuracy of placement of the modules.

The full crown system of this invention satisfies function and esthetics with two independent modules combined to form one functional and esthetic unit. In addition, there is no known combination of separate modules that permits such a simplified, accurate and inexpensive full crown procedure. Further, this modular crown system can be adapted to work in combination with partial denture prostheses. The functional metallic module can be specially preformed to receive routine or precision clasping devices for partial dentures.

Practice of this system requires the provision of the usual range of size, shape and coloring of the modules in order to meet the normal variations encountered in restoring coronal area.

FIGS. 1 and 2 show the functional module 10 and the esthetic module 20, respectively. Module 20 is of an esthetic material over at least its outer surfaces. Module 20 is composed either wholly of the esthetic material, or of esthetic material overlying a metallic substructure. Module 20 amounts to a full cap which provides the mesial, distal, lingual and incisal surfaces for the full crown. Module 10 of metal provides the wear surfaces for the full crown.

Modules 10 and 20 include mating surfaces which assist in locating and securing the modules together. Module 20 includes female member 24 located on the outside of module 20 into which is fitted male member 14 located on the inside of module 10. Module 20 also has a shoulder 22 against which abuts edge 12 of module 10. Module 20 also has a surface 26 which is shaped to conform to surface 36 that is prepared on tooth stump 30 for that purpose.

The natural tooth of the patient is prepared for the crowns of this invention according to procedures for full crowns which are well-known to the art, and no additional or different procedures need by learned by the practitioner. A properly prepared anterior tooth is shown at 30 in FIG. 3. The correct size and shape of the functional and esthetic modules needed for the prepared tooth are established by observation and/or measurement. The cervical (gingival) border of the crown members is trimmed to adapt to the prepared tooth. Then a conventional plastic mix or fill, with a catalyst to provide controlled hardening, is placed in the crown and the crown is fitted to the prepared tooth. Excess fill material which is extruded from the crown during the fitting procedure is trimmed away and the margins are defined. The crown is then cemented in place in accordance with standard operating procedures.

Splinting of prefabricated esthetic crowns of this invention is shown in FIG. 4 for a missing anterior tooth. It should be understood that the procedures for splinting posterior teeth are essentially the same as described hereinafter for the anterior teeth. Two or more prefabricated crowns 40 and 40 of this invention are provided for prepared teeth 30 and 30. The crowns, including a dummy tooth 42, are fitted to the patient and the facings are luted with a suitable wax.

An impression is made with a rigid material such as French's plaster to cover the lingual surface in the anterior area and the lingual and occlusal in posterior area. The facings are removed from the backings. To the exposed interior surface of the backings is poured a refractory material. When the refractory material is hard, the original plaster-type impression material is removed. This leaves the backings accurately related and held by the hardened refractory material. The backings are combined by a suitable solder and then broken free of the refractory material. The facings are replaced in their correct positions. The fill is placed on the interior of the prefabricated veneer crowns and the direct placement procedure is followed. The foregoing may be accomplished with a model of the prepared teeth in relation to each other as in the indirect assembly technique.

The normal chairside practice of this two module system is as follows:

1. After determining correct size, shape and coloring, the esthetic module is filled with a self curing plastic mix (or other suitable autocure material) and fitted to the prepared tooth stump.
2. After trimming excess and fitting margins, the esthetic module is permanently cemented.
3. The functional module is placed in position. Articulation with the opposing dentition is checked and adjusted as necessary.
4. The functional module is cemented in position to complete the operation.

In the case of splinting, adjacent functional modules are soldered or welded together prior to cementation of the functional modules onto the esthetic modules.

An indirect approach to handling this system follows:

1. An impression of the prepared tooth/teeth and registration of the articulation.
2. Model poured and mounted in relation to the opposing dentition.
3. The esthetic module(s) are fitted to the prepared teeth and processed as acrylic crown(s).
4. The completed esthetic modules are cemented to the prepared tooth/teeth.
5. The functional module(s) is/are placed in position. Articulation with the opposing dentition is checked and adjusted as necessary.
6. The functional module(s) is/are cemented in position.

In the case of splinting, adjacent functional modules are soldered or welded prior to cementation. In splinting procedures, the accuracy of the soldering or welding of the functional modules is simplified since the esthetic module is cemented in position and the exact position of the functional modules can be extremely accurately registered before welding or soldering.

In bridging procedures, the use of a dummy tooth composed of a functional and esthetic module is utilized. The esthetic module of this member is solid and can be modified to adapt to the ridge of the edentulous area. The procedure is as follows:

1. The esthetic modules are cemented to the prepared adjacent teeth by the method described for individual crowns.
2. The esthetic module of the dummy member is fitted to the edentulous area and luted to the adjacent esthetic modules with an autocure material.
3. The functional modules are placed, adjusted for proper occlusion, registered in their final positions with a suitable material.
4. A model is poured in a refractory material. After hardening, the functional modules are soldered or welded.
5. The functional modules are cemented in final position.

The functional modules of this system are composed of metal; stainless steel is preferable and should be approximately 0.5 mm in thickness.

The esthetic modules are composed of an easily manipulated esthetic material; acrylic plastic is preferable. The portion of the esthetic module which is adapted to receive the functional module should be about 0.25 mm in thickness. The surfaces of module 20 that are not to be mated to functional module 10 are thicker than the mated surfaces.

The two modules are separable and should remain separable until the final cementation of the functional module to the esthetic module.

What is claimed is:

1. A prefabricated full crown system comprising two separate modules joined to form a unitary crown adapted to be mounted on and surround a prepared tooth stump to be capped, one of said modules is a functional module of metal and covers the mesial, distal, lingual, incisal or occlusal surfaces of the fully constructed unitary crown, the other of said modules is an esthetic module full cap having at least outer surfaces of plastic and covering all of the exposed surfaces of said prepared tooth stump when mounted thereon, said esthetic module is fitted to said prepared tooth stump independently of said functional module and has prepared areas on at least one of the mesial, distal, lingual, incisal or occlusal surfaces to receive said functional module, the portion of said esthetic module underlying said functional module in said fully constructed unitary crown being thinner than the other surfaces of said esthetic module.

2. The modular crown system of claim 1 wherein said esthetic module is wholly of acrylic material.

3. The modular crown system of claim 1 wherein a plurality of said functional modules are welded or soldered to join or splint adjacent members.

4. The modular crown system of claim 1 wherein a modular pontic or dummy tooth is soldered or welded to the adjacent of said modular crowns to effect replacement of a missing tooth.

5. The modular crown system of claim 1 wherein said functional module is modified to permit precision partial clasping or attachment.

* * * * *